(12) United States Patent
Tellex et al.

(10) Patent No.: US 11,383,386 B2
(45) Date of Patent: Jul. 12, 2022

(54) ROBOTIC DRAWING

(71) Applicant: Brown University, Providence, RI (US)

(72) Inventors: Stefanie Tellex, Cambridge, MA (US); Atsunobu Kotani, Providence, RI (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 17/282,567

(22) PCT Filed: Oct. 3, 2019

(86) PCT No.: PCT/US2019/054519
§ 371 (c)(1),
(2) Date: Jul. 14, 2021

(87) PCT Pub. No.: WO2020/072785
PCT Pub. Date: Apr. 9, 2020

(65) Prior Publication Data
US 2022/0032468 A1     Feb. 3, 2022

Related U.S. Application Data

(60) Provisional application No. 62/741,323, filed on Oct. 4, 2018.

(51) Int. Cl.
| | |
|---|---|
| B25J 13/08 | (2006.01) |
| B25J 9/16 | (2006.01) |
| B25J 11/00 | (2006.01) |
| B25J 15/00 | (2006.01) |
| G06V 30/32 | (2022.01) |

(52) U.S. Cl.
CPC ......... B25J 9/1697 (2013.01); B25J 11/0075 (2013.01); B25J 13/08 (2013.01); B25J 15/0019 (2013.01); G06V 30/32 (2022.01)

(58) Field of Classification Search
CPC ...... B25J 9/1697; B25J 11/0075; B25J 13/08; B25J 15/0019; B25J 11/00; G06V 30/32; A61F 2/72
See application file for complete search history.

(56) References Cited

U.S. PATENT DOCUMENTS

| | | | |
|---|---|---|---|
| 9,665,259 B2 * | 5/2017 | Lee | G06F 3/0412 |
| 2002/0064308 A1 * | 5/2002 | Altman | G06V 10/768 |
| | | | 382/187 |
| 2005/0069205 A1 | 3/2005 | Khomo | |

(Continued)

FOREIGN PATENT DOCUMENTS

WO     2019094867 A2     5/2019

OTHER PUBLICATIONS

Kwok et al., Evolutionary Replication of Calligraphic Characters By A Robot Drawing Platform Using Experimentally Acquired Brush Footprint, 2006, IEEE, p. 466-471 (Year: 2006).*

(Continued)

*Primary Examiner* — McDieunel Marc
(74) *Attorney, Agent, or Firm* — Adler Pollock & Sheehan P.C.

(57) ABSTRACT

A method includes providing a robot, providing an image of drawn handwritten characters to the robot, enabling the robot to capture a bitmapped image of the image of drawn handwritten characters, enabling the robot to infer a plan to replicate the image with a writing utensil, and enabling the robot to reproduce the image.

5 Claims, 5 Drawing Sheets

(56) References Cited

U.S. PATENT DOCUMENTS

2013/0275091 A1    10/2013   Peterson et al.
2017/0277367 A1*    9/2017   Pahud ................. G06F 3/04883
2017/0340459 A1    11/2017   Mandelbaum

OTHER PUBLICATIONS

Kwok et al., Genetic Algorithm-Based Brush Stroke Generation for Replication of Chinese Calligraphic Character, 2006, IEEE, p. 1057-1064 (Year: 2006).*

Hood et al., When Children Teach a Robot to Write: An Autonomous Teachable Humanoid Which Uses Simulated Handwriting, 2015, IEEE, p. 83-90 (Year: 2015).*

Li et al., Human-like robotic handwriting and drawing, 2013, IEEE, p. 4942-4947 (Year: 2013).*

Muto et al., Inter-Personal Interaction for Handwrite Training ~ A Study for Development of Handwrite Skill Training Robot 2009, IEEE, p. 1173-1178 (Year: 2009).*

Osaki et al., Embodied Navigation for Mobile Robot by Using Direct 3D Drawing in the Air, 2008, IEEE, p. 671-676 (Year: 2008).*

Safdari et al., A Hierarchical Feature Learning for Isolated Farsi Handwritten Digit Recognition Using Sparse Autoencoder, 2016, IEEE, p. 67-71 (Year: 2016).*

Portillo et al., Haptic Desktop for Assisted Handwriting and Drawing, 2005, IEEE, p. 512-517 (Year: 2005).*

Hood et al., "When Children Teach a Robot to Write: An Autonomous Teachable Humanoid 1-3 Which Uses Simulated Handwriting", ACM, Mar. 31, 2015, pp. 83-90.

Boren Li, "Human-like Robotic Handwriting and Drawing", Dec. 31, 2012, 52 pages.

International Search Report and Written Opinion received in International Application No. PCT/US2019/054519 dated Jan. 22, 2020, 14 pages.

A. Kotani and S. Tellex, "Teaching Robots To Draw," 2019 International Conference on Robotics and Automation (ICRA), 2019, pp. 4797-4803, doi: 10.1109/ICRA.2019.8793484.

* cited by examiner

FIG. 5

ROBOTIC DRAWING

CROSS REFERENCE TO RELATED APPLICATIONS

This application is a national phase filing under 35 U.S.C. § 371 of International Application No. PCT/US2019/054519 filed Oct. 3, 2019, which claims benefit from U.S. Provisional Patent Application No. 62/741,323, filed Oct. 4, 2018, the entire contents of which are hereby incorporated by reference herein.

STATEMENT REGARDING GOVERNMENT INTEREST

This invention was made with government support under grant number IIS-1652561 awarded by the National Science Foundation. The government has certain rights in the invention.

BACKGROUND OF THE INVENTION

The present invention relates generally to robotics, and more particularly to robotic drawing.

In general, robotics is a branch of technology which deals with robots. Robots are programmable machines which are usually able to carry out a series of actions autonomously, or semi-autonomously. Robots can interact with the physical world via sensors and actuators, robots are programmable and robots are usually autonomous or semi-autonomous.

Industry-specific robots can perform several tasks such as picking and placing objects, and movement adapted from observing how similar manual tasks are handled by a fully-functioning human arm. Such robotic arms are also known as robotic manipulators. These robotic manipulators were originally used for applications concerning bio-hazardous or radioactive materials or use in inaccessible places. In order to collaborate with humans, one would like a manipulator robot to be able to draw on a white board, write a message with a pen on a post-it note, or draw a diagram. The ability to write would enable a robot to put up a sign directing people that a hallway was closed, to produce art using physical mediums such as a paint brush or a pen, or to address and mail a letter. Additionally, the robot could potentially engage in teaching activities at a white board, writing a math equation or drawing a diagram. These skills rely on the ability to produce a policy to draw with a writing utensil. Artificial Intelligence (AI) is still a long way from replicating a human-like writing or drawing skills. Given the complexity of human hand movement not to forget other factors like the speed of each stroke and spacing, it is difficult for a robotic arm to do the job elegantly.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In general, in one aspect, the invention features a method including providing a robot, providing an image of drawn handwritten characters to the robot, enabling the robot to capture a bitmapped image of the image of drawn handwritten characters, enabling the robot to infer a plan to replicate the image with a writing utensil, and enabling the robot to reproduce the image.

In another aspect, the invention features robotic manipulator including an arm and body including joints connected by large links and configures to move and place objects or tools within a workspace, a wrist including two or three compact joints and configured to arrange the objects or tools at the workspace, a camera, a controller, and a processor and a memory, the memory including a process which enables the robotic manipulator to write handwritten characters or line drawings.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

These and other features, aspects, and advantages of the present invention will become better understood with reference to the following description, appended claims, and accompanying drawings where:

FIG. 5 illustrates a demonstration of a second robot reproducing a target image.

DETAILED DESCRIPTION

Figure 1:
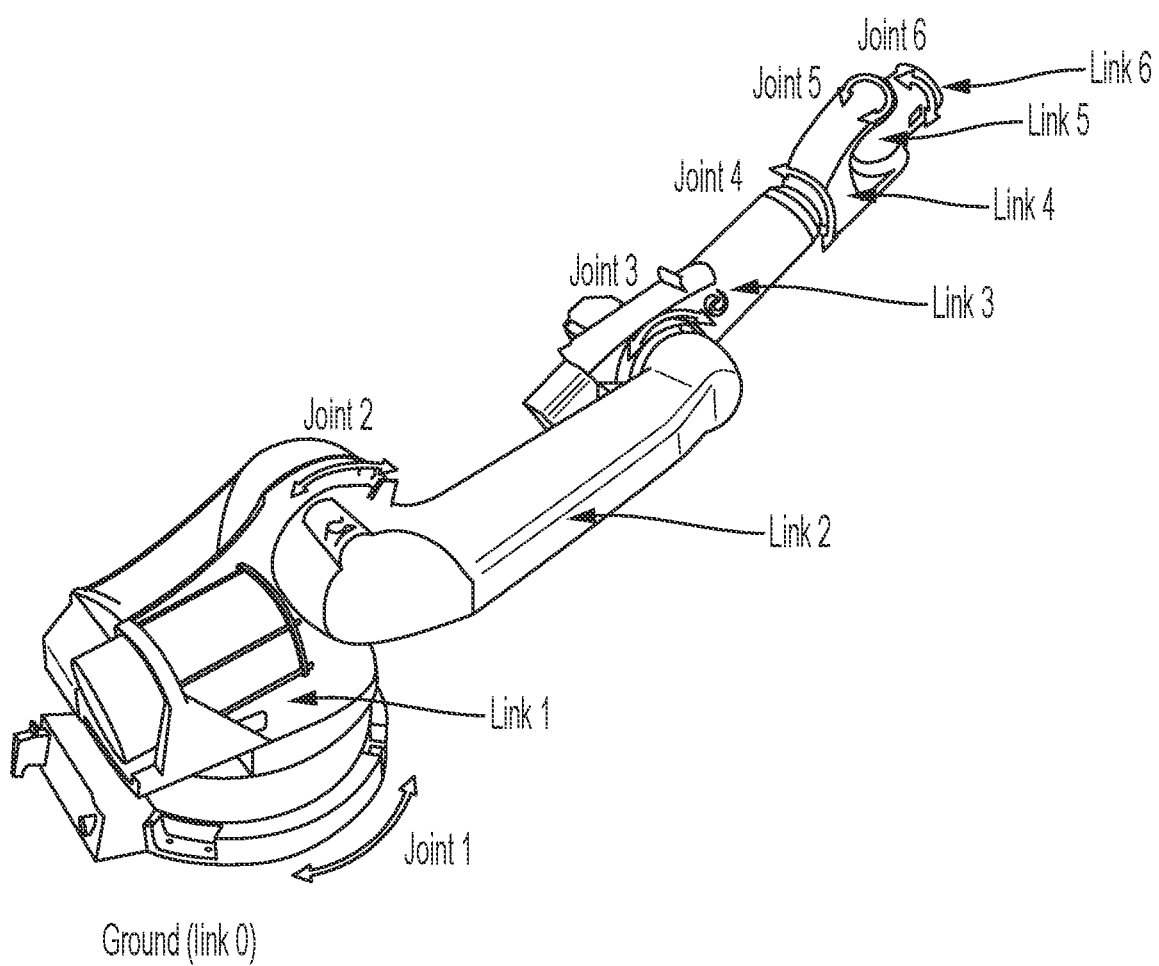
FIG. 1 is diagram of an exemplary robot manipulator.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

In FIG. 1, an exemplary robot manipulator 10 is illustrated. In general, a robot manipulator is an electronically controlled mechanism, including multiple segments, that performs tasks by interacting with its environment. They are also commonly referred to as robotic arms.

Manipulators such as robot manipulator 10 are composed of an assembly of links and joints. Links are defined as the rigid sections that make up the mechanism and joints are defined as the connection between two links. A device attached to the manipulator which interacts with its environment to perform tasks is called an end-effector (i.e., link 6 in FIG. 1). Other components, such as a camera, processor and memory, may also be included in the robot manipulator 10.

Shown an image of handwritten characters, robots should draw each target stroke in one consecutive drawing motion. Existing methods for robots that write with a utensil are unable to look at a bit-mapped image and directly produce a drawing policy. Instead, they require external information about the stroke order for character, such as human gestures or predefined paths for each letter. This extra information makes it challenging for novice users to teach the robot how to draw new characters, because the stroke order information must be provided. A more recent reinforcement learning based approach successfully learns to draw the target image, yet their model still struggles to draw each target stroke in one continuous drawing motion, and frequently draws the same parts over and over to replicate the target image.

Methods of the present invention, in contrast, take as input an image to draw, then generate commands for robots to replicate the image with a writing utensil. The method divides the drawing problem into two scales: 1) the local scale, consisting of a 5×5 pixels window, and 2) the global scale, consisting of the whole image. The method trains two separate networks for the different scales. Unlike other approaches, the present method does not require any pre-defined handcrafted rules, and learns drawing from stroke-order demonstrations provided only during its training phase.

The methods of the present invention can look at a bitmap image of a character that a robot has not previously seen and accurately reproduce the character. In almost all instances our method also predicts the correct stroke order and direction for the character. In addition, methods of the present invention enable two different robots to draw characters on paper and on a white board in at least ten different languages as well as stroke-based drawings, including English, Chinese, French, Greek, Hindi, Japanese, Korean, Tamil, Urd and Yiddish.

Figure 2:
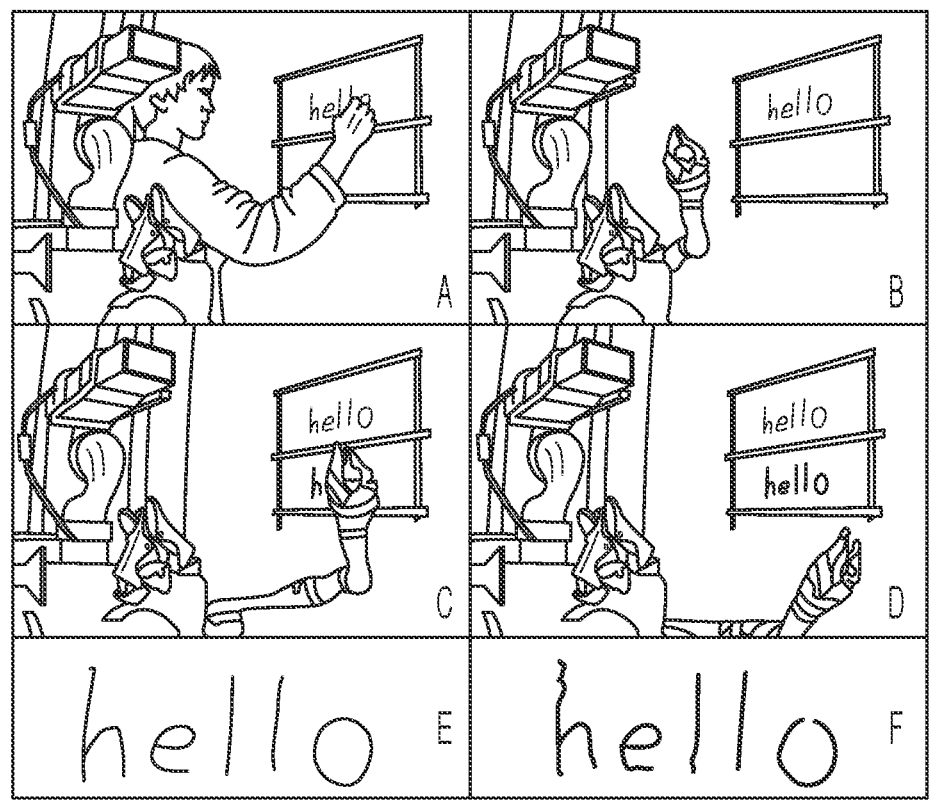
FIG. 2 illustrates an example of a robot reproducing the English word "hello."

FIG. 2 illustrates an example of a robot reproducing the English word "hello." More specifically, A) shows a user drawing characters on a whiteboard, B) shows a robot taking a bitmapped image from its camera, C) shows the robot executing commands predicted by the present invention in real-time, D) shows the finished process, E) shows an image of the user's drawing, and F) shows an image of the robot's drawing.

In the present invention, given the target image of a handwritten character, $X^{target}$, the goal is to generate a sequence of actions, $A=\{a_1, a_2, \ldots, a_L\}$, for a robot to reproduce $X^{target}$. Here we define $X^{target}$ as a 100×100 binary image, and a command at timestep t as $a_t=(\Delta x, \Delta y, touch)$ where $\Delta x$ and $\Delta y$ are shifts in x, y coordinates that range between −100 and +100. The variable touch is a boolean value which controls the touch/untouch status of a writing utensil with respect to a canvas.

One aim is to train a parametrized function approximator $f_\theta$ such that $A=f_\theta(X^{target})$. While it is possible to directly estimate θ, dividing the problem into two sub-problems and separately training two specialized distinct models achieves better performance. The first sub-problem is to make the agent follow each stroke from its start to end. A Local Model is designed with parametrized weights $\theta_L$ for this task. The second sub-problem is to predict the starting location of the next stroke at the end of current stroke. A Global Model with weights $\theta_G$ is designed. The local model predicts where to move itself next in its 5×5 pixel environment. Once it reaches to an end, the global model predicts the next starting point of the new stroke. This process is repeated iteratively until the entire target image is visited, and obtain the full action sequence $A=\{a_1^G, a_1^L, a_1^L, \ldots, a_n^L, a_m^G, a_{n+1}^L, \ldots\}$.

Figure 3:
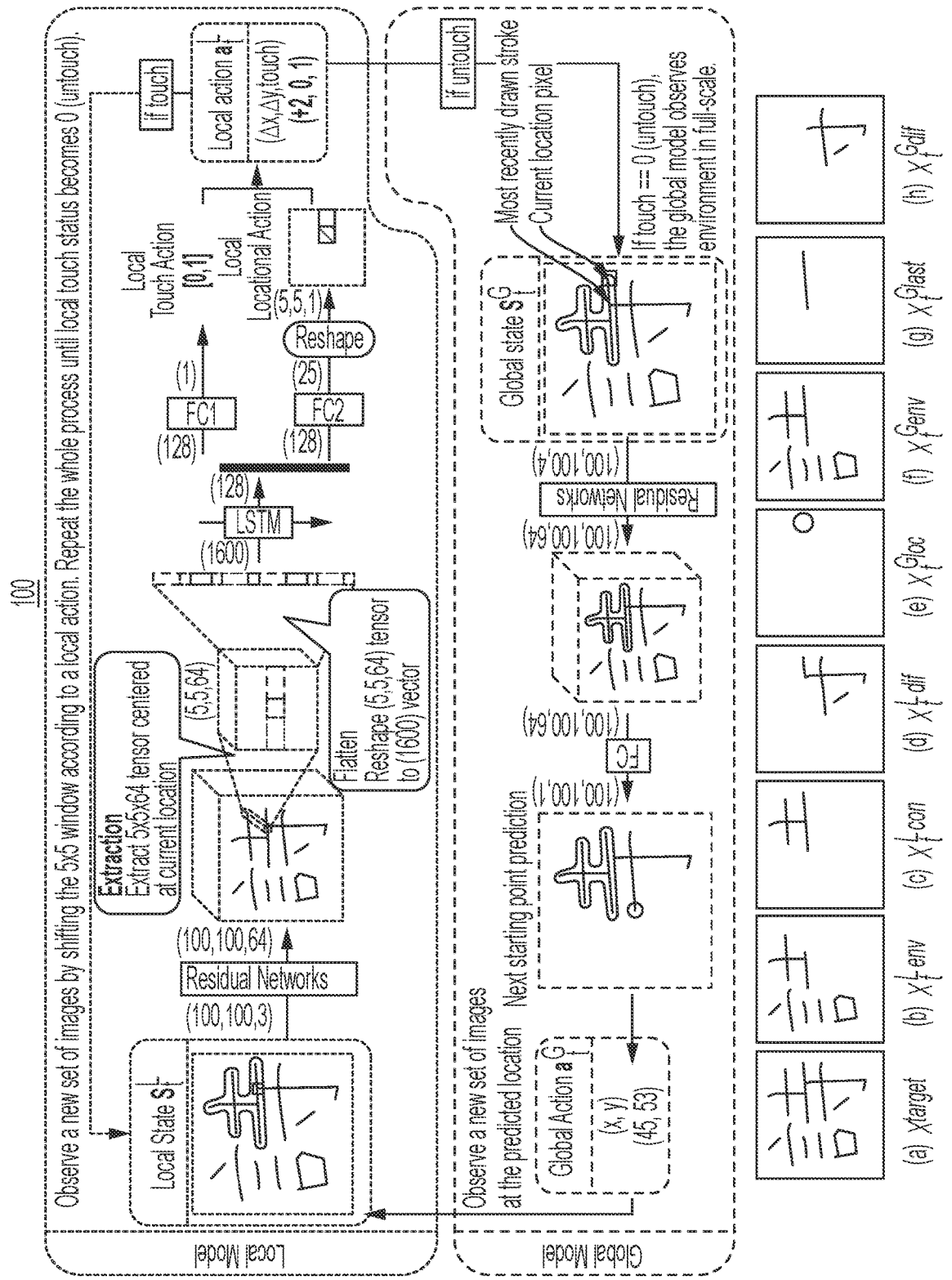
FIG. 3 illustrates an exemplary network architecture.

FIG. 3 illustrates an exemplary network architecture 100 of the present invention. The network 100 includes two sub-models, a local model and a global model, where "FC" stands for a fully-connected layer. The local state $s_t^L$ is a combination of $(X_t^{Lenv}, X_t^{Lcon}, X_t^{Ldif})$, and the global state $s_t^G$ is a combination of $(X_t^{Gloc}, X_t^{Genv}, X_t^{Glast}, X_t^{Gdif})$.

Given a starting point, a goal of the local model is to follow a stroke until it reaches an end. A local state at time stamp t, $s_t^L$, is a set of three images.

1) $X_t^{Lenv}$: already visited by the local model ((b) in FIG. 3),

2) $X_t^{Lcon}$: target region continuously connected with a current location of the local model ((c) in FIG. 3), 3) $X_t^{Ldif}$: difference image between target image $X^{target}$ and $X_t^{Lenv}$, which is the unvisited region of the target image ((d) in FIG. 3).

A unique characteristic of the local model design is that an extraction procedure is applied to the encoded tensor of shape (100, 100, 64) to extract the (5, 5, 64) tensor centered at the current location of the agent. The reasons why local information is extracted are:

1) Generalization of knowledge: Every image of handwritten characters is different, and in order to gain general knowledge of drawing, it is crucial to work in smaller scale where an agent will encounter similar situations more frequently.

2) Computational Expensiveness: Feeding large images directly into RNN (recurrent neural networks) to predict a sequence of actions is computationally expensive. By extracting a small region, the size of input tensors to RNN cells is drastically reduced which achieves less computational expense and faster training.

3) Information selection: While the agent draws a stroke, the most important region to focus on is mostly the one around the current position. In a broad view, the local network can be seen as a structural attention mechanism where we force our model to attend to the 5×5 local region around the current location.

In order to preserve continuity in drawing actions, a Long Short-Term Memory (LSTM) is used in the local network. As a simple example, when the agent reaches the intersection of two lines, it has choices of going either North, South, East, or West. If we know that the agent came from the North, we can make a reasonable guess that it should go South in order not to disrupt the continuity of the drawing motion. All past actions matter to predict the next action, and we use LSTM to capture this context.

Now, we formally define how our local network predicts the next action $a_t^L$. Given a local state at timestep t as $s_t^L$ and current location as $(x_t, y_t)$, our local model first encodes the input tensor, $s_t^L$ using residual networks:

$$e_t^L = f_{\theta LResidual}(s_t^L) \quad (1)$$

The residual networks include four residual blocks, each of which contains two sub-blocks of 1) batch normalization layer, 2) rectified linear unit, and 3) two-dimensional convolutional layer. Convolution layers in these four blocks have channels of [[16, 16], [16, 16], [16, 32], [32, 64]], stride of 1, width of 3 and height of 3. After the residual networks layer, we have an encoded tensor $e_t^L$ of shape (100, 100, 64), and we then apply the extraction procedure to $e_t^L$ centered at $(x_t, y_t)$ and receive a new tensor, $e_t^{L*}$ with shape (5, 5, 64).

To feed $e_t^{L*}$ into the LSTM, we reshape it into a vector $v_t^L$ of length 5×5×64=1600:

$$v_t^L = \text{reshape}(e_t^{L*}) \quad (2)$$

We feed $v_t^L$ to the LSTM and receive context vector $c_t^L$ and hidden state representation $h_t^L$ as:

$$c_t^L, h_t^L = f_{\theta LLSTM}(s_t^L)([v_t^L, h_{t-1}^L]) \quad (3)$$

Two components of local action $a_t^L$, the local touch action $a_t^{Ltouch}$ and the location action $a_t^{Lloc}$ are calculated from the context vector $c_t^L$:

$$a_t^{Ltouch} = \sigma(f_{\theta LFC1}(c_t^L))$$

$$a_t^{Lloc} = \text{argmax } f_{\theta LFC2}(c_t) \quad (4)$$

Where σ is a sigmoid function, Finally, the loss function of the local model is given as:

$$L^{Local} = -1/N \Sigma_t^N \log(f_{\theta L}(s_t^L)) a_t^{L*} \quad (5)$$

where $a_t^{L*}$ is the true target action provided during training.

A goal of the global model is to predict a starting point of the next stroke in a full-scale image. When $a_t^{Ltouch}=0$, the global model observes a current state $s_t^G$, which is a set of four images.

1) $s_t^{Gloc}$: current location of the local model ((e) in FIG. 3),
2) $s_t^{Genv}$: already visited region by the local model ((f) in FIG. 3),
3) $s_t^{Glast}$: recently visited region by the local model since the last global prediction ((g) in FIG. 3),
4) $s_t^{Gdif}$: difference image between target image $X^{target}$ and $X_t^{Gdif}$.

The global network also has the residual network to encode state images, and it shares all weights with the one in the local model, except for the very first initialization layer. To adjust the channel size of input tensors, the initialization layer in our residual network maps a tensor of shape (N, N, M) to (N, N, 16). Due to the discrepancy in shapes between local and global states, the size of the layer is different. We obtain the global action $a_t^G$ as:

$$e_t^G = f_{\theta GResidual}(s_t^G)$$

$$c_t^G = f_{\theta GFC}(s_t^G)$$

$$a_t^G = \text{argmax } e_t^G$$

$$(x,y) \quad (6)$$

and the loss function for the global model is:

$$L^{Global} = -1/M \Sigma_t^M \log(f_{\theta G}(s_t^G)) a_t^{G*} \quad (7)$$

where $a_t^{G*}$ is the target next start location which is provided during training.

To illustrate the system of the present invention works in various robotic environments, it was tested with two robots. We directly applied our trained model to the real robotic environment, which creates a need to reprocess the original target image to match the image format of our training data, such that the line width has to be 1, and the image has to be size of 100×100, and so on. If our model sees a vertically-long one-stroke drawing, for example, it is likely to divide the stroke region into squared regions, individually solve the drawing for each window, and combine the results together once all completed. To adjust the line width, we used a skeletonization technique which extracts the center line of stroke-based drawing.

First Robot (Herein Referred to as "Baxter")

Figure 4:
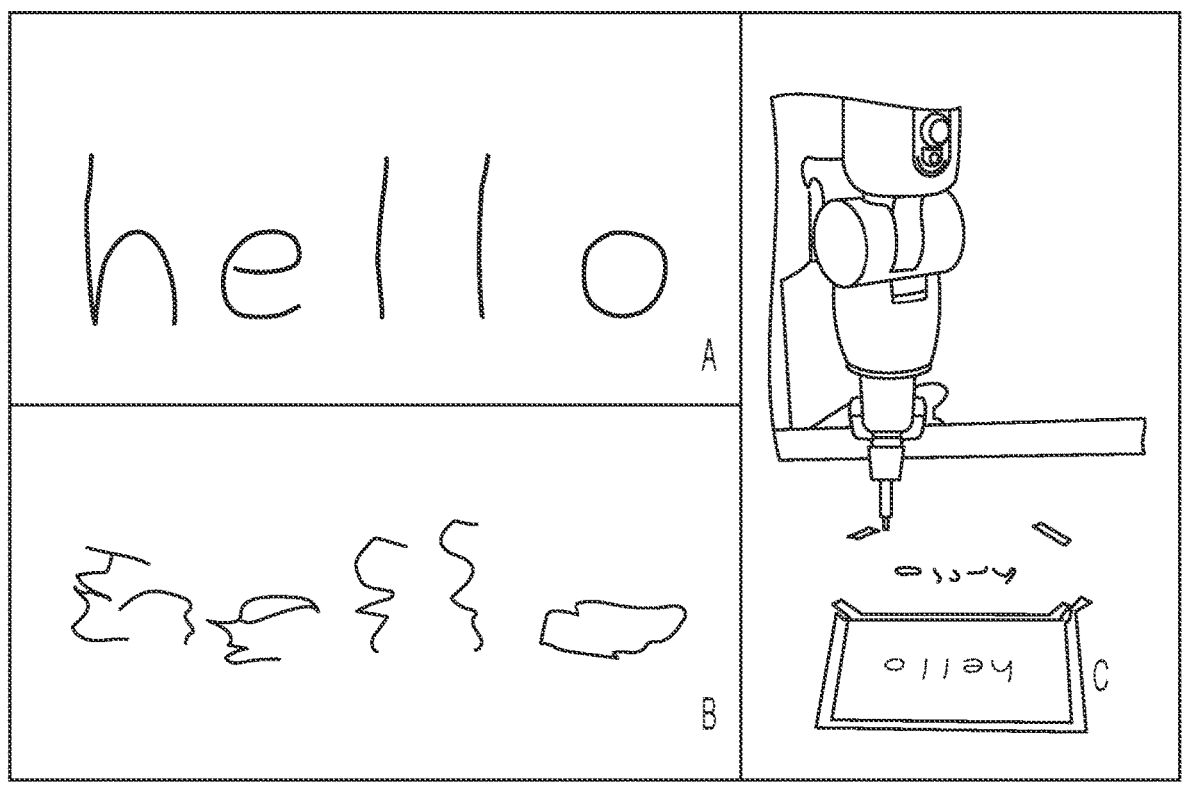
FIG. 4 illustrates a demonstration of a first robot reproducing a target image.

As shown in FIG. 4, Baxter first takes an image of a hand drawn black-on white characters from its wrist camera. It then generates relevant commands and starts drawing on paper with its marker, which we rigidly attached to the gripper. The drawn characters reproduce the input characters and general appearance. However there is still significant error in the drawn characters due to errors in the movement of the Baxter. This error is due to position errors in the robot's end effector due to the series elastic design of the robot arm.

In summary, (A) shows the target image that Baxter tried to replicate, (B) shows the image drawn by Baxter, and (C) shows Baxter in motion.

Second Robot (Herein Referred as "MOVO")

We tested our model on a MOVO robot, using a Kinova Jaco arm and the Kinect 2 as a sensor. With its precise movement capabilities MOVO reproduces the target image very accurately. Overall, the robot demonstration produces a policy for drawing recognizable characters, including languages such as Greek, Hindi and Tamil, which were previously seen during training. Photographs of drawn and handwritten examples appear in FIG. 5.

More specifically, the word "Hello" is show in different languages: from the top—English cursive, Urdu, Greek, Japanese, Korean, Chinese, Tamil, French, Hindi and Yiddish, and a sketch of the Mona Lisa. Strokes on the left are hand-drawn on a white board; strokes on the right are drawn by the robot on the same white board after viewing the input image on the left.

Figure 5:
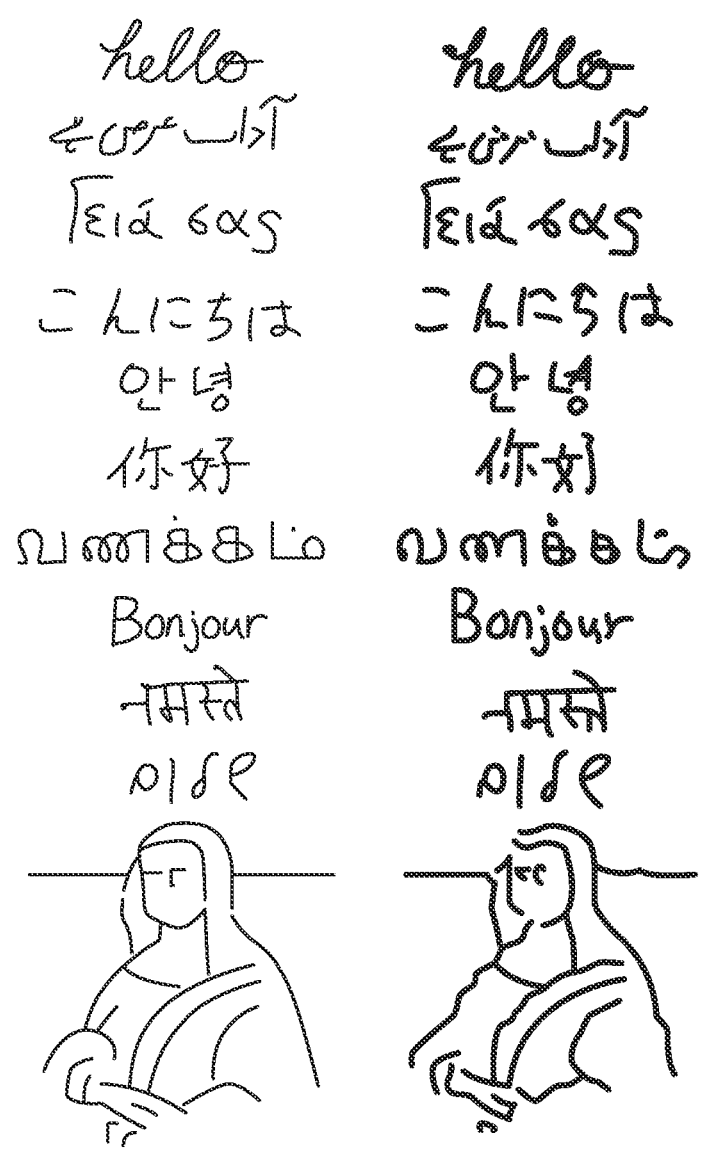

The accuracy of our model's ability to reproduce English cursive, as shown in FIG. 5, raises the question of the ability of this framework to reproduce handwritten signatures. For example, given an image of a signature, our approach could infer a policy for reproducing that signature with a pen held by a robot. This capability has ramifications in areas where signatures written with a writing utensil are used to verify agreement, such as legal documents.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A method comprising:
    providing a robot;
    providing an image of drawn handwritten characters to the robot;
    enabling the robot to capture a bitmapped image of the image of drawn handwritten characters;
    enabling the robot to infer a plan to replicate the image with a writing utensil; and
    enabling the robot to reproduce the image;
    wherein enabling the robot to reproduce the image comprises enabling the robot to draw each target stroke in one continuous drawing motion to write from a dataset of demonstrations;
    wherein enabling the robot to reproduce the image comprises providing the robot commands to execute predicted by a model in real time; and
    wherein the robot commands comprise:
        commands to make the robot follow each stroke from its start to end; and
        commands to predict a starting location of a next stroke at an end of a current stroke.

2. The method of claim 1 wherein the commands to make the robot follow each stroke from its start to end are derived from a local model.

3. The method of claim 2 wherein the local model predicts where to move itself next in its 5×5 pixel environment.

4. The method of claim 3 wherein the commands to predict the starting location of the next stroke at the end of the current stroke are derived from a global model.

5. The method of claim 4 wherein the global model predicts the next starting point of the new stroke in a full-scale image plane.

\* \* \* \* \*